United States Patent [19]

Durbin

[11] 4,386,642
[45] Jun. 7, 1983

[54] UNIVERSAL PORTABLE PACK

[76] Inventor: William H. Durbin, P.O. Box 416, Redwood City, Calif. 94064

[21] Appl. No.: 212,328

[22] Filed: Dec. 2, 1980

[51] Int. Cl.³ .................... A45C 11/00; A45C 13/02
[52] U.S. Cl. .................... 150/34; 150/52 R; 190/51; 206/570
[58] Field of Search ............... 150/34, 52 J, 30, 52 R; 190/51, 60, 43; 206/570, 803

[56] References Cited

U.S. PATENT DOCUMENTS

| | | | |
|---|---|---|---|
| 1,266,091 | 5/1918 | Basch | 190/43 |
| 1,653,246 | 12/1927 | Zichy | 190/51 X |
| 1,834,740 | 12/1931 | Rhett | 190/43 |
| 2,648,366 | 8/1953 | Higbee et al. | 150/34 |
| 3,110,376 | 11/1963 | Naab et al. | 190/51 |
| 3,381,782 | 5/1968 | Ikelheimer | 190/51 |
| 3,874,435 | 4/1975 | Allen | 150/30 X |
| 3,981,398 | 9/1976 | Boshoff | 206/570 |
| 4,169,550 | 10/1979 | Williams | 190/52 X |
| 4,212,377 | 7/1980 | Weinreb | 190/52 |
| 4,260,004 | 4/1981 | Domke | 150/30 |

FOREIGN PATENT DOCUMENTS 2373988 7/1978 France .................... 150/34

Primary Examiner—William T. Dixson, Jr.
Assistant Examiner—Sue A. Weaver
Attorney, Agent, or Firm—Leonard R. Cool

[57] ABSTRACT

A carrying case or portable pack is constructed in the form of an attache case. A tray storage area providing receptacles for separately holding relatively long and narrow objects is releasably attachable to the inner surface of the lid and flat bulk storage is provided between the base of the tray and said inner surface. A holding material is attached along the inner side walls of the base and individual pockets, for separate package storage, have a surface material mounted on the exterior thereof which permits releasable attachment to said holding material. The pouches or pockets may vary in size, thus permitting flexibility in storing the packaged materials. In addition, the pouches may be coded, as by color coding, for rapid identification and selection of items to be used for a particular function, for example in a medical procedure.

4 Claims, 5 Drawing Figures

UNIVERSAL PORTABLE PACK

BACKGROUND OF THE INVENTION

This invention relates generally to selective storage of items in a portable pack and, more particularly, but not as a limitation, to storage of apparatus for use in emergency medical procedures.

A carrying case is disclosed in U.S. Pat. No. 3,381,782 in which partitioning members are used for generating compartments of various sizes and shapes in the base portion of the case. While such an arrangement permits reposition of the partitioning members to establish space sizes to fit a variety of items, it does not permit the prepackaging, quick release and attachment, nor does it include storage in the lid as taught by the instant invention.

In U.S. Pat. No. 3,981,398 an aid in the management of medical procedures is disclosed in which the base of a briefcase is set up as a tray-like receptacle with recesses containing a drug or instrument or other article in each recess. Selection of the drug(s) or instrument(s) is accomplished by placing the appropriate one of a plurality of masks over the tray-like receptacle. Each mask has openings over only those instruments and/or drugs to be used in the selected procedure. Further, the masks include a summary of the medical procedure steps. Disadvantages of such a tray and mask arrangement include the limitation of the materials that may be stored, the problems of mask alignment as well as the possibility that the wrong mask may be selected.

An emergency medical kit is disclosed in U.S. Pat. No. 4,169,550. This kit consists essentially of a back pack which has been especially arranged to carry emergency medical equipment. However, such a kit does not permit the rapid selection and replacement of items, nor does it provide the ease of accessibility which is necessary in emergencies and which is possible by use of the pack described herein.

SUMMARY OF THE INVENTION

An attache type case is arranged to provide tray-like storage in the lid. The tray has a base which is releasably attachable to the inner surface of the lid. Thus bulk storage of relatively flat items is provided between the base of the tray and the inner surface of the lid in addition to the tray storage. The bottom of the case includes fastening means, and pouches are available for separately storing items in the bottom. The pouches are provided with means for attachment to the fastening means so that each pouch is separately, releasably, attachable to the bottom.

DETAILED DESCRIPTION OF THE INVENTION

Figure 1:
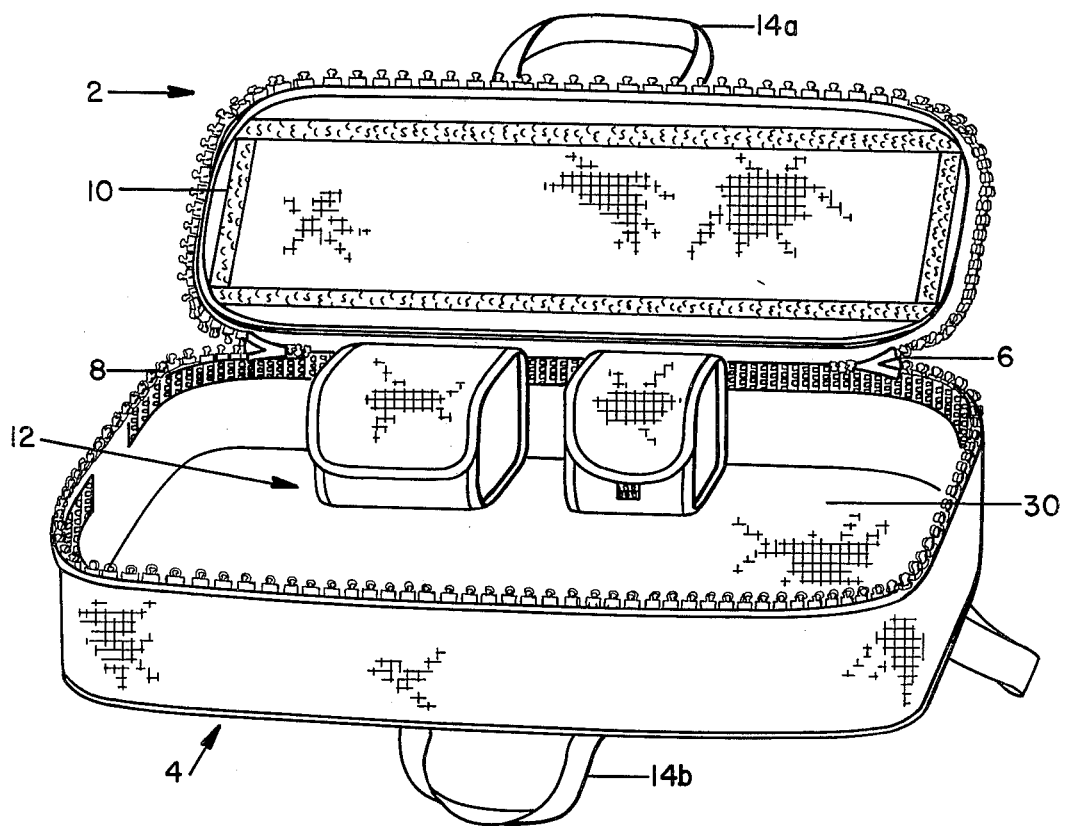
FIG. 1 is an isometric view of the portable pack in which the pack is open to show the interior features.

Referring now to FIG. 1 there is seen a case in the form similar to that of an attache case having a lid portion 2 and a bottom portion 4 connected together along a common edge 6. Although the case is shown open so that the lid and bottom are at right angles one to the other, it should be understood that this was done only for purposes of illustration. In a preferred embodiment, the case is formed out of a heavy duty material such as, for example, 1000 Denier Dupont Cordura Nylon; and it is the material which provides the common edge 6 as well as the necessary hinge effect. Thus, the lid and bottom portions may be, and usually are, opened so that each lies approximately in parallel planes. This provides better access to the materials stored therein. When closed, normal locks may be employed. Further, the lid and bottom material may be formed of a heavy duty plastic, rather than the pliable nylon. In a preferred embodiment, the lid and bottom are secured together by means of zippers, as shown in FIG. 1, which slide from each side of the hinged portion toward the front where handles 14 are located.

Figure 2:
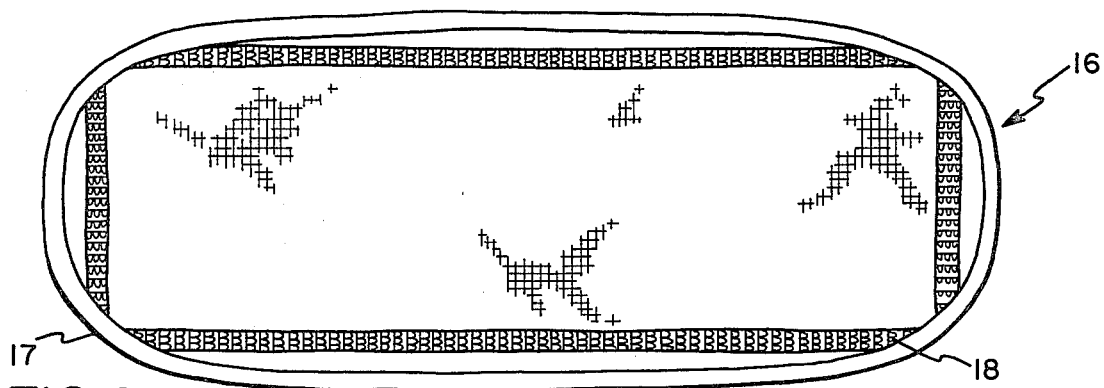
FIG. 2 is a back view of the lid storage member illustrating the manner in which this member is releasably attachable to the lid.
Figure 3:
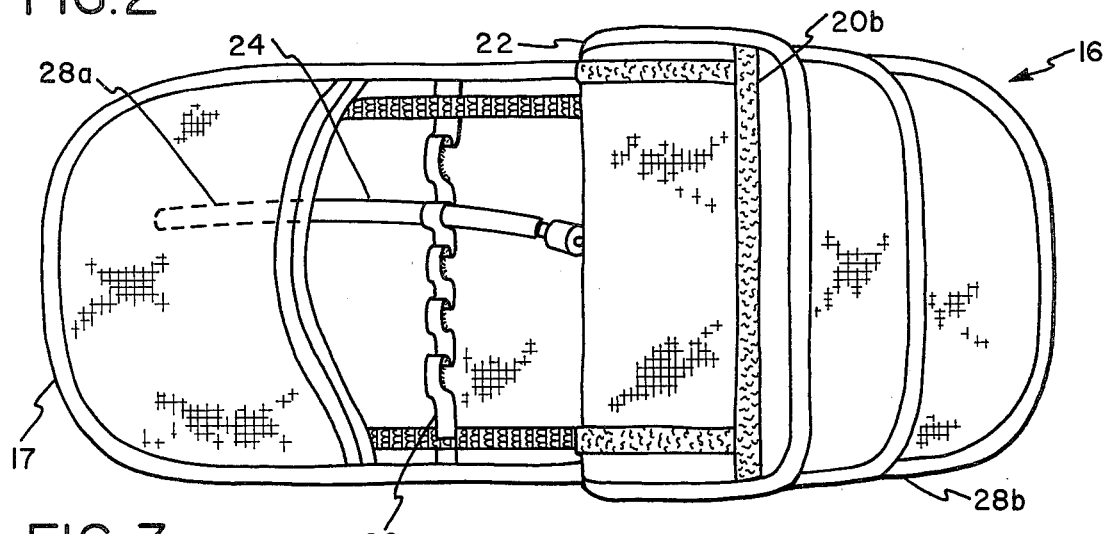
FIG. 3 is a front view of the lid storage member illustrating how one of a pair of storage pouches, each of which contain adjustable guides for holding relatively flat items, form a tray for holding the items in separate, adjacent locations, thus providing for easy selection and removal.

The depth of the lid is variable and is designed to provide adequate space for storage tray 16, FIG. 2, which provides pouch 28a as shown at the left of tray 16 in FIG. 3 in which items 24 are stored. A second pouch 28b is located at the right of the tray 16 and provides storage facilities which are similar to those provided in pouch 28a. Flap 22 is a protective cover for items 24 and is secured by means of holding strips 20b, which may be of a material such as VELCRO. Flap 22 is shown open over pouch 28a and closed over pouch 28b. For medical emergency use, items 24 may consist of assorted endotracheal tubes, oral and nasal airways and/or assorted syringes. The guides 26 are adjustable so they may be adapted to fit any of a variety of tubing and similar devices. This may be accomplished by the use of a VELCRO fastner (not shown) having one portion attached to the pouch near one side and approximately at the center of the pouch area, and having the other end free so that the size and location of the guides may be adjusted.

Referring again to FIG. 1, the inner surface of the lid 2 has a holding strip 10 which may be made of VELCRO or some similar holding material. A matching strip of the holding material is mounted on the back of base 17. This is shown at 18 in FIG. 2. When the tray is attached to the inner surface of lid 2, a recess is formed between the inner surface of lid 2 and the base 17. Thus, flat storage is provided, and such storage may be used in an emergency medical pack, for example, for pressure bandages and the like. It provides suitable flat storage for other types of items when the pack is used for other purposes.

The bottom of the pack is made deeper than the lid to permit storage of bulkier items. In order to allow the user the opportunity to select particular items or groups of items package storage is employed by means of pouches 12 as shown in FIG. 1. Two different sized pouches are illustrated to highlight the flexibility of storage available. Of course, the bottom could literally be covered with pouches, but such are not shown in order to permit clarity of exposition. It should be understood, however, that a plurality of such pouches, in a variety of sizes, may in fact be employed. The size and disposition would be dependent upon the material to be carried. From the foregoing, it is clear that such a pack could be readily adapted for carrying the lenses, filters, film, etc., required by a professional photographer, as well as for many other uses. In the preferred of the invention in which the outer shell is made up from heavy duty nylon, a plastic tub is inserted in the bottom, and forms a protective shield for the materials stored in the pouches 12. The plastic tub is not shown separately, but it is understood that it fits skin tight in the bottom section of the pack. Normally the tub is retained by the tight fit. In one case, the tub was fitted with holes through which the straps for back packing where inserted, thus providing a fixed holding means. Also for medical use, the tub may be equipped with a recessed mount and retaining straps for an oxygen D cylinder. This is most readily done by locating the cylinder in the center of the pack and having the pouches 12 attached along the interior side walls. As noted, the pack may not only be provided with carrying handles 14, but may also be arranged to permit its being carried on the back of the packer.

Figures 4A, 4B:
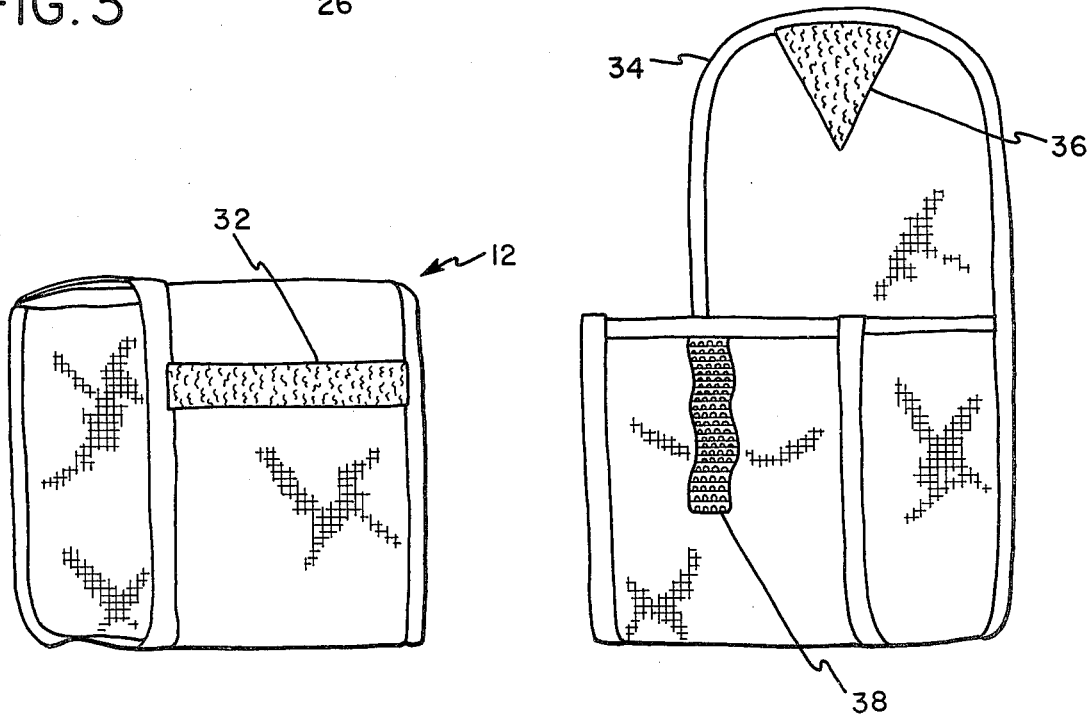
FIG. 4A is a back view of a pouch for storing items in the bottom of the case.
FIG. 4B is a front view of the pouch of FIG. 4A illustrating how the flap 34 has fastening material 36 mounted on the interior side thereof for locking engagement with the material 38 on the exterior of the pouch.

Whether or not a plastic tub is used, a holding strip, as shown at 8, FIG. 1, is provided. Note that the holding strip is mounted along the side walls near the upper edge of the bottom portion. It has been found that this is a desirable position, because it seems to provide better holding power. Of course, the holding strip could be otherwise located. As shown in FIG. 4A, the back of each pouch 12 has a corresponding holding strip 32 mounted so that the pouch strips will mate with the bottom strips when the pouch is resting on the interior surface 30 of the bottom 4. As noted hereinabove, pouches 12 may be made in a variety of sizes, but must fit within the depth of the side walls of bottom 4. Each pouch will have a flap 34 at the open end thereof which will permit closure. Thus, items stored in each pouch will be held separately and each will be easily selected from those stored in the bottom 4. The flaps are each provided with a holding strip 36. The corresponding holding strip is shown at 38, and as illustrated in FIG. 4B the strip is of sufficient length so as to permit flexibility in the tightness of the seal when the flap is in the closed position. Thus, the closure can be adjusted so as to properly fit the item(s) stored in the pouch.

Another important feature is that the pouches may be coded, for example by the use of distinctive colors, so that those items which are most commonly used together, or which must be used together, are readily identified. Since this coding can be accomplished under rational conditions, a minimum of errors should be made in the original coding. This should be reflected in improved performance even where a pack such as this is to be used for emergency medical treatment.

Although the pack has been described with respect to a particular embodiment thereof, it is clear that a number of changes could be made which would not depart from the spirit and intent of the invention. For example, the lid could be reinforced so as to provide a more rigid structure, thus giving greater protection to the flat material stored between the storage tray and the inner surface of the lid. Further, the tray which attaches to the lid could be made in a number of different shapes to fit the objects to be stored. With respect to the bottom, the pouches could be attached by using holding strips located in a position other than that shown. For example they could be located along the inner surface of the bottom adjacent the side walls. It will be understood by those skilled in the art that other changes in form and detail may be made without departing from the spirit and scope of the invention.

As could be understood from the foregoing discussion the pack size will depend upon the particular use to which it is to be adapted. Where portability is a factor, the size and weight must be necessarily limited. In one such application, the pack size was set for a cardio respirator application. The size was approximately six inches deep, fourteen inches wide and twenty four inches long. The pack carried the following: oxygen "D" cylinder, demand valve and mask, B.P. cuff, stethoscope, nasal cannula, oxygen extension tubing, oxygen mask, assorted endotracheal tubes, esophogeal obturator airway, oral and nasal airways, assorted syringes, bite stick, 2-500 cc D5W intravenous solutions, 2-microdrop intravenous tubings, assorted intravenous catheters, 3-sodium bicarbinates, 2-epinephring 1:10000, 2-dopamine, 2-Isuprel, 1-lidocaine 100 mg, 1-lidocaine 2 Gm.

What is claimed is:

1. A portable pack having a structure similar to an attache case in that there is a relatively thin lid portion and a thick or deep bottom portion which are hinged together along one side, and which may be fully opened so that both lid and bottom portions face in the same direction, thereby permitting ready acess to the contents therein, the pack comprising:
    a tray for holding relatively flat, long articles which is adapted for releasable attachment to the inner surface of said lid portion, said tray comprising:
    a flat support member having on one side thereof means adapted for releasable attachment to said lid, and on the other side thereof receptacles for positioning article to be transported, so that they are readily available when needed, said receptacles comprising a VELCRO fastener having one portion attached to the pouch near the center area, and having the other section free so that the size and location of the positioning receptacles may be changed to accomodate different sized articles for transport;
    a heavy duty nylon pouch having the opposite ends thereof sealed closed for protecting the other ends of said positioned articles, having the center open when said cover is in the open position, and having the receptacles placed at the open area for ease of storage of said positioned articles;
    a cover for protecting the positioned articles when not in use; and
    means for attaching said cover to the other side of said support member so as to cover said positioned articles;
    a continuous holding strip mounted along the perimeter of the interior sides of the bottom portion;
    a plurality of storage pouches of varying sizes, each having holding strips on the back thereof, said strips being adapted to mate with holding strips of the interior surfaces of said bottom portion, so that these pouches may be rapidly removed and secured in any desired location within the interior of said bottom portion.

2. Apparatus as set forth in claim 1 wherein said storage pouches comprise:

a heavy duty material shaped like a box having four sides and an opening at the top, and with a bottom, and having a flap at the top which extends from one side, the flap having a length which is greater than the length of the bottom so that the flap will easily extend beyond the side opposite from said extended side, said flap having a VELCRO fastening strip attached near the flap edge; and a VELCRO fastening strip along said side opposite so as to facilitate opening and closing of the pouch.

3. Apparatus as set forth in claim 2 wherein said pouches holding strip comprises a VELCRO strip attached to one side, not including said opposite side, and arranged to mate with the holding strip on the interior of said bottom portion.

4. Apparatus as set forth in claim 3 wherein said holding means comprises:

a VELCRO strip attached to the interior of said bottom portion for attachment to a mating strip on each said pouch.

* * * * *